United States Patent
Tsai et al.

(10) Patent No.: US 6,201,151 B1
(45) Date of Patent: Mar. 13, 2001

(54) PROCESSES FOR PREPARING OPTICALLY ACTIVE (S)-α-ARYL PROPIONIC ACID OR ESTER THEROF

(75) Inventors: Shau-Wei Tsai; Chun-Sheng Chang, both of Tainan (TW)

(73) Assignee: National Science Council of Republic of China (TW)

( * ) Notice: Subject to any disclaimer, the term of this patent is extended or adjusted under 35 U.S.C. 154(b) by 0 days.

(21) Appl. No.: 09/213,188

(22) Filed: Dec. 17, 1998

(51) Int. Cl.⁷ .............................. C07C 55/28; C07C 1/04
(52) U.S. Cl. .......................... 562/489; 435/280; 560/60
(58) Field of Search ...................... 562/489; 435/280; 560/60

(56) References Cited

U.S. PATENT DOCUMENTS

| | | | |
|---|---|---|---|
| 3,637,767 | * 1/1972 | Alvarez | 549/554 |
| 4,565,782 | * 1/1986 | Bewick | 435/122 |
| 4,744,948 | * 5/1988 | Incorvia | 422/7 |
| 4,762,793 | * 8/1988 | Cesti et al. | 435/280 |
| 4,886,750 | * 12/1989 | Bertola et al. | 435/136 |
| 5,273,895 | * 12/1993 | Rossi et al. | 435/136 |
| 5,912,164 | * 6/1999 | Warneck et al. | 435/280 |

FOREIGN PATENT DOCUMENTS

WO 97/34860 * 9/1997 (WO) .

* cited by examiner

*Primary Examiner*—Gary Geist
*Assistant Examiner*—Taylor V Oh
(74) *Attorney, Agent, or Firm*—Drum & Roth

(57) ABSTRACT

A process for preparing an optically active (S)-α-aryl propionic acid, by hydrolyzing a racemic thioester of α-aryl propionic acid at various temperature in different aqueous organic solvents in the presence of an (S)-stereoselective lipase to form an (S)-α-aryl propionic acid product, while the unreacted (R)-thioester of α-aryl propionic acid can be converted to the corresponding (S)-thioester of α-aryl propionic acid via a racemization reaction by adding a base as the catalyst in the solution and then hydrolyzing by the lipase described as above so that the (S)-α-aryl propionic acid can be obtained theoretically at a conversion of 100% and with high optical purity. The invention also relates to a process for preparing an optically active (S)-α-aryl propionic acid ester, by adding separately additional alcohol in said various organic solvents and carrying out the transesterification of a racemic thioester of α-aryl propionic acid to form an (S)-α-aryl propionic acid ester product, while the unreacted (R)-thioester of α-aryl propionic acid can be converted to the corresponding (S)-thioester of α-aryl propionic acid via a racemization reaction by means of the base added in the solution as the catalyst and then transesterifying again by the lipase as described above so that an (S)-α-aryl propionic acid ester product can be obtained at, theoretically, a conversion of 100% and with high optical purity.

8 Claims, 5 Drawing Sheets

PROCESSES FOR PREPARING OPTICALLY ACTIVE (S)-α-ARYL PROPIONIC ACID OR ESTER THEROF

BACKGROUND OF THE INVENTION

1. Field of the invention

The invention relates a process for preparing an optically active (S)-α-aryl propionic acid, by hydrolyzing a racemic α-aryl propionic acid thioester at various temperature in different aqueous organic solvents in the presence of an (S)-stereoselective lipase to form an (S)-α-aryl propionic acid product, while the unreacted (R)-α-aryl propionic acid thioester can be converted to the corresponding (S)-α-aryl propionic acid thioester via a racemization reaction by adding a base as the catalyst in the solution and then hydrolyzing by the lipase described as above so that the (S)-α-aryl propionic acid can be obtained theoretically at a conversion of 100% and with high optical purity. The invention also relates to a process for preparing an optically active (S)-α-aryl propionic acid ester, by adding separately additional alcohol in said various organic solvents and carrying out the transesterification of a racemic thioester of α-aryl propionic acid to form an (S)-α-aryl propionic acid ester product, while the unreacted (R)-α-aryl propionic acid thioester can be converted to the corresponding (S)-α-aryl propionic acid thioester via a racemization reaction by means of the base added in the solution as the catalyst and then transesterifying again by the lipase as described above so that an (S)-α-aryl propionic acid ester product can be obtained at, theoretically, a conversion of 100% and with high optical purity.

2. Description of the prior art

α-Aryl propionic acids, known as profens, as shown in following formula (I), are non-steroid inflammatory drugs (NSAIDs) having effects of analgesic, antipyretic and antiflammation. A variety of such type of drugs is commercially available such as ibuprofen (1), naproxen (2), ketoprofen (3), flurbiprofen (4) and the like. According to an estimate [Ahuja, 1997], the yearly total sale of the first three drugs was in an amount of three billion US dollars which indicates commercial values thereof and hence has been developed in effort by a number of drug manufactures and research institutes.

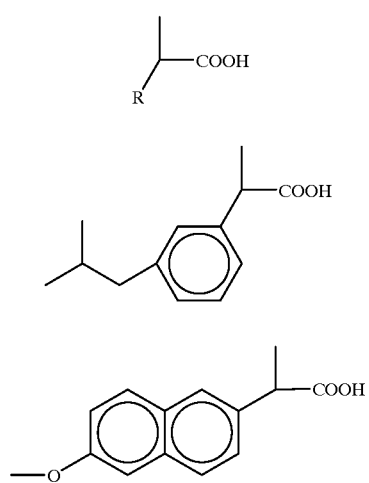

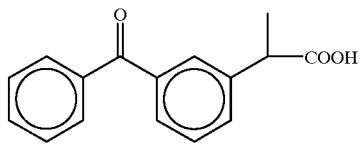

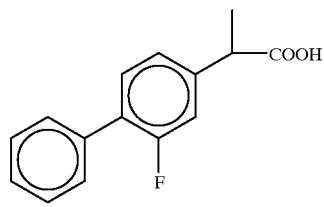

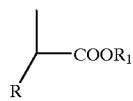

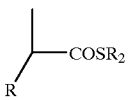

wherein, R is an aryl group: R1 and R2 are substitutes.

α-Aryl propionic acid has enantiomers of R and S configurations with not entirely the same pharmalogical effects each other in an organism. For example, the pharmacological effect of the (S)-isomer of naproxen is 28-fold that of the (R)-isomer thereof, whereas the pharmacological effect of the (S) ibuprofen is 100-fold or more higher than that of its R isomer. Under the increasingly severe requirement of regulation for drug control, drugs marketed in the form of racemates at present will be required invariably to be soled in an optically pure form and under such circumstance, the preparation of optically active drugs by an efficient process to meet the commercial demand will be more emphasized. Further, the past study has shown that oral administration of (S)-α-aryl propionic acid products might cause side effects of gastrointestinal bleeding or ulcer [Shanbhag et al., 1992], so that it becomes a common object in effort to develop prodrugs of the (S)-form ester (II) or amide derivative of the α-aryl propionic acid in order to lower the toxicity induced by the acid functionality of the α-aryl propionic acid. Methods for obtaining optically active substances include those described as follows [Sheldon, 1993]: (1) synthesis from naturally occurring optically active precursors; (2) asymmetrical or asymmetrically induced syntheses from prochiral compounds by using biocatalysts such as microorganisms, enzymes, and the like or asymmetrical metallic catalyst; and (3) resolution of racemates, comprising chromatography, diastereomeric salt crystallization, preferential crystallization and kinetic resolutions by using biocatalysts or diastereomeric metallic catalysts. For example, commercial processes for preparing (S)-naproxen are based mainly on diastereomeric salt crystallization of salt formed with bases such as methylphenylamine and the like, and on the asymmetrical synthesis by using asymmetrical metallic catalysts.

Recently, due to the advancing by leaps and bounds of enzymatic engineering techniques, processes involve carrying out hydrolysis or transesterification resolution on racemic ester of α-aryl propionic acid [Chest, 1986; Palmer et al., 1993; Sigh et al., 1988; Sigh, 1986], as well as the esterification resolution on racemic α-aryl propionic acid [Mertoli et al., 1996; Mustranta, 1992; Tsai et al., 1994 ] in the presence of organic solvents by using esterases or lipases having high stereoselectivity.

However, no matter which resolution method was used to resolve racemates, theoretically, only at most 50% of the desired optically active product can be obtained thereby. In contrary, the inventor of this application has developed a process for preparing (S)-α-aryl propionic acid or (S) esters thereof by carrying out hydrolysis or transesterification dynamic resolution on racemic thioester of α-aryl propionic acid compounds (III) in the presence of organic solvents by using both of lipase and base as catalysts, characterized in that it can break through the 50% yield limit of the desired optically active products and obtain the 100% of theoretical conversion. Since, no one has reported in the literature regarding the application of such a process for preparing (S)-α-aryl propionic acid or (S) ester thereof, the process according to the invention is a novel process and is also a practical process in view of the high optical purity and conversion higher than 50% of the product obtained thereby.

SUMMARY OF THE INVENTION

Accordingly, it is an object of the invention to provide a process for preparing an optically active (S)-α-aryl propionic acid, by hydrolyzing a racemic thioester of α-aryl propionic acid at various temperature in different aqueous organic solvents in the presence of an (S)-stereoselective lipase to form an (S)-α-aryl propionic acid product, while the unreacted (R)-α-aryl propionic acid thioester can be converted to the corresponding (S)-α-aryl propionic acid thioester via a racemization reaction by adding a base as the catalyst in the solution and then hydrolyzing by the lipase described as above so that the (S)-α-aryl propionic acid can be obtained theoretically at a conversion of 100% and with high optical purity.

The another object of the invention is to provide a process for preparing an optically active (S)-α-aryl propionic acid ester, by adding separately additional alcohol in various microaqueous organic solvents and carrying out the transesterification of a racemic thioester of α-aryl propionic acid to form an (S)-α-aryl propionic acid ester product, while the unreacted (R)-α-aryl propionic acid thioester can be converted to the corresponding (S)-α-aryl propionic acid thioester via a racemization reaction by means of the base added in the solution as the catalyst and then transesterifying again by the lipase as described above so that an (S)-α-aryl propionic acid ester product can be obtained at, theoretically, a conversion of 100% and with high optical purity.

BRIEF DESCRIPTION OF THE DRAWINGS

The invention, as well as its many advantages, may be further understood by the following detailed description and drawings in which.

DETAILED DESCRIPTION OF THE PREFERRED EMBODIMENT

Figure 1:
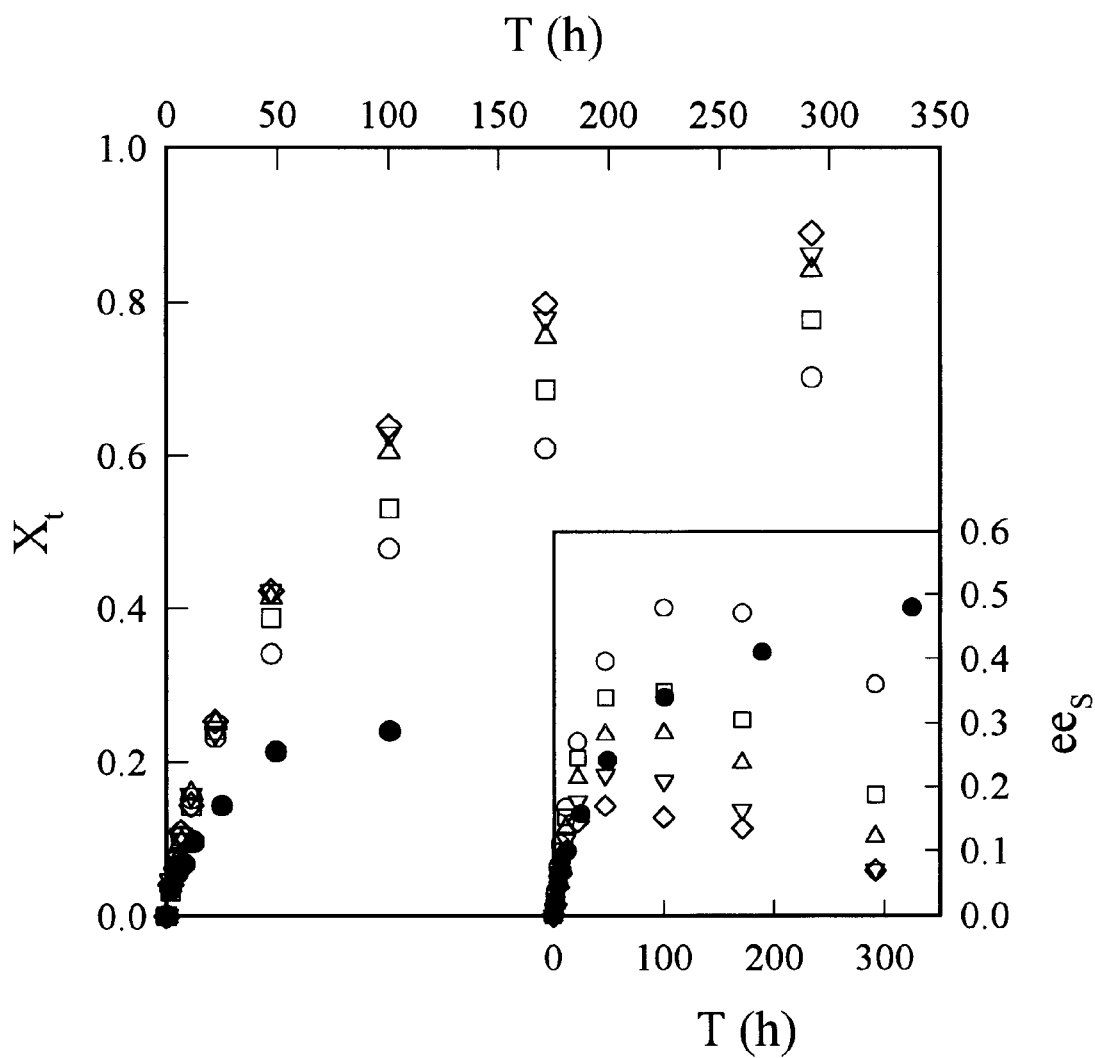
FIG. 1 is a diagram showing the time-course variation of $ee_S$ and $X_t$ at different concentrations of trioctylamine: 0 mM, (●); 25mM, (○); 50mM, (□); 75mM, (Δ); 100 mM, (▽); 125mM, (◇).

As stated above, the invention provides a process for preparing an optically active (S)-α-aryl propionic acid or (S)-ester thereof, by hydrolyzing a racemic thioester of α-aryl propionic acid at various temperature in different aqueous organic solvents in the presence of an (S)-stereoselective lipase to form an (S)-α-aryl propionic acid product, while the unreacted (R)-α-aryl propionic acid thioester can be converted to the corresponding (S)-α-aryl propionic acid thioester via a racemization reaction by adding a base as the catalyst in the solution and then hydrolyzing by the lipase described as above so that the (S)-α-aryl propionic acid can be obtained theoretically at a conversion of 100% and with high optical purity. Similarly, by adding separately additional alcohol in said various organic solvents and carrying out the transesterification of a racemic thioester of α-aryl propionic acid to form an (S)-α-aryl propionic acid ester product, while the unreacted (R)-α-aryl propionic acid thioester can be converted to the corresponding (S)-α-aryl propionic acid thioester via a racemization reaction by means of the base added in the solution as the catalyst and then transesterifying again by the lipase as described above so that an (S)-α-aryl propionic acid ester product can be obtained at, theoretically, a conversion of 100% and with high optical purity As noted above, α-aryl propionic acids or their ester prodrugs thereof have effects of analgesic, antipyretic and anti-flammation. The racemic thioester compounds can be obtained firstly by conventional chemical synthetic methods. In order to obtain (S)-α-aryl propionic acid or (S)-ester prodrugs thereof , the process according to the invention comprises carrying out hydrolysis or transesterification of said thioester in the presence of organic solvent by means of lipase having (S)-stereoselectivity, and at the same time, carrying out the racemization of the residual (R)-α-aryl propionic acid thioester compound by means of the base added as catalyst, and thus obtains a product with high optical purity and at a theoretical conversion of more than 50% instead of the maximum conversion of 50% that conventional resolution methods can only obtain.

Lipases suitable for the process of the invention can be selected from various microorganism sources, including , but not limited to, *Aspergillus niger, Candida rugosa, Geotrichum candidum, Pseudomonas cepacia, Rhizopus oryzae* and the like, and the lipase derived from Candida rugosa is the preferred.

Racemic α-aryl propionic acid thioester compound suitable for the process according to the invention may include, for example, thioester compounds of ibuprofen, naproxen, ketoprofen, flurbiprofen and the like, and the thioester compound of naproxen is the preferred.

Organic solvents suitable for the process according to the invention may include, for example, isooctane, heptane, hexane, cyclohexane, pentane, toluene, benzene and the like, and isooctane or cyclohexane is preferable.

Bases suitable for the process according to the invention may include, for example, organic bases such as triethylamine, tributylamine, trioctylamine and the like, and anion-exchange resins such as those obtained by modification of IRA 904 anion-exchange resin produced by Sigma Co., USA, and trioctylamine and anion-exchange resin bearing AcO⁻ are preferable.

The following examples will illustrate the feasibility and practicability of the process according to the invention, but not to limit the scope thereof. All those regarding the technique of the invention, that is, a process for preparing optically active (S)-α-aryl propionic acids (profens) or esters thereof hydrolyzing or transesterifying a racemic α-aryl propionic acid thioester in the presence of an (S)-stereoselective lipase, a base catalyst and organic solvents will be encompassed within the scope of the appended claims of the invention.

EXAMPLE 1

Figure 2:
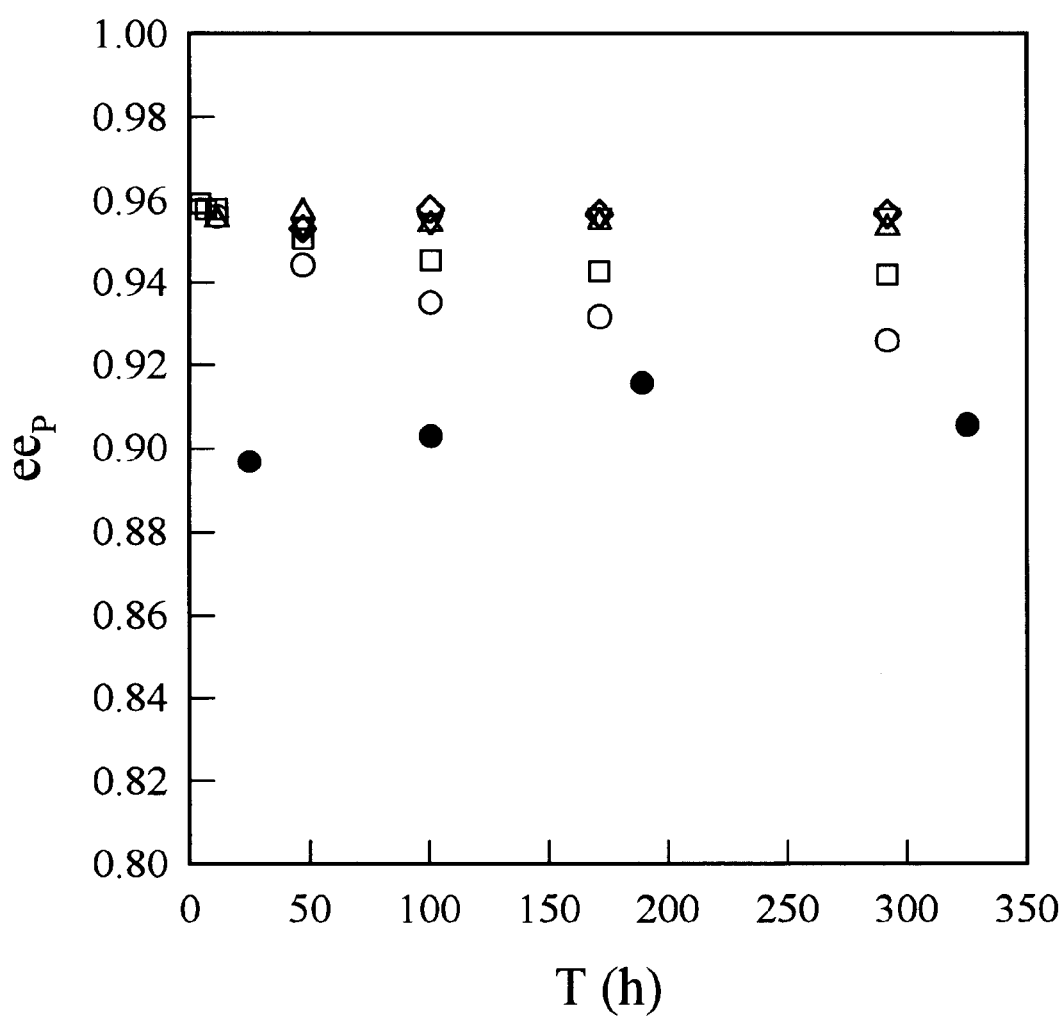
FIG. 2 is a diagram showing the time-course variation of $ee_P$ at different concentrations of trioctylamine ( meanings of symbols are same as in FIG. 1).

A series of 15 ml isooctane solution was prepared as containing 3 mM of racemic naproxen trifluoroethyl thioester, 20 mg/ml of Lipase MY (triacylglycerol ester hydolases, EC 3.1.1.3, having activity of 108 mmole/mg/h, provided by Meito Sangyo Co., Japan) and different concentrations of trioctylamine for carrying out hydrolytic dynamic resolution at 45° C., or containing no trioctylamine for performing hydrolytic resolution. By taking samples at various time intervals and analyzed by high performance liquid chromatography ( mobile phase composition as n-hexane:isopropanol:acetic acid=97:3:1; flow rate=0.4 ml/min, on a Chiralcel OD column provided by Daicel Co., Japan) to obtain time-course variations of the conversion of the racemate ($X_t$), optical purity of the reactant ($ee_S$) and optical purity of the product ($ee_P$) as shown in FIGS. 1 and 2, wherein $X_t$, $ee_S$ and $ee_P$ are defined as $$X_t = \frac{P+Q}{A+B+P+Q}$$

$$ee_s = \frac{A-B}{A+B}$$

$$ee_p = \frac{P-Q}{P+Q}$$

wherein A and B represent (S)-and (R)-naproxen trifluoroethyl thioester, respectively, while P and Q represent concentrations of (S)-and (R)-naproxen, respectively.

Results indicate that, increasing trioctylamine concentration could increase the reaction rate of the racemic naproxen trifluoroethyl thioester and the degree of racemization for the (R)-thioester such that, in the same reaction time period, $ee_S$ would lower whereas $X_t$ increased. In addition, $ee_P$ of the product could keep always at greater than 95%. In the case of reaction time for 290 hours, the addition of trioctylamine system could in general break through the bottleneck of 50% conversion of (S)-naproxen. Compared with the conventional resolution process which does not add trioctylamine, the process of the invention does increase the conversion of racemate $X_t$ and the $ee_P$ of the product and hence establishs the feasibility and practicability of the invention.

EXAMPLE 2

Figure 3:
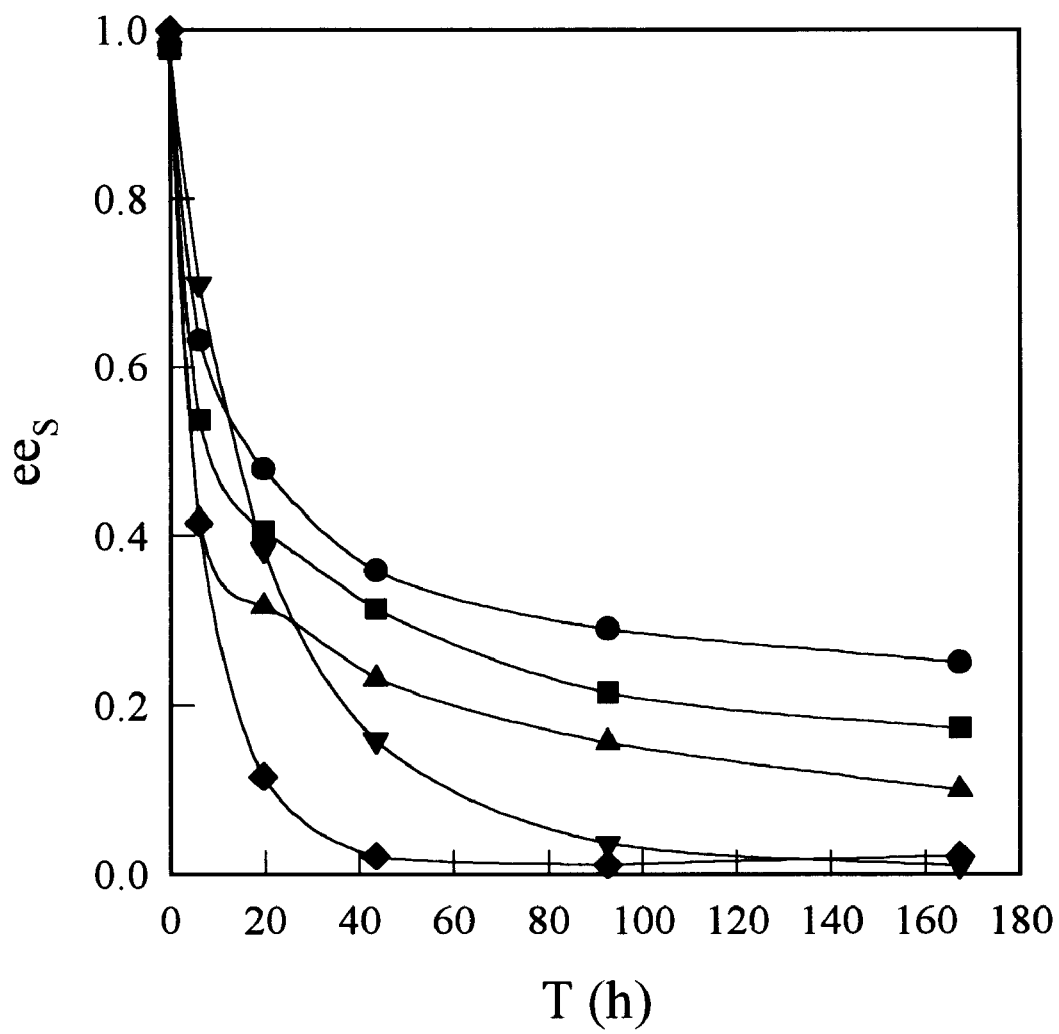
FIG. 3 is a diagram showing the time-course variation of $ee_S$ of (S)-naproxen trifluoroethyl thioester in isooctane; modified IRA 904 anion-exchange resin bearing : OH⁻ group (●); AcO⁻ group (▼) ; $CO_3^{-2}$ group(■); $HCO^{-3}$ group (▲); trioctylamine (◆).
Figure 4:
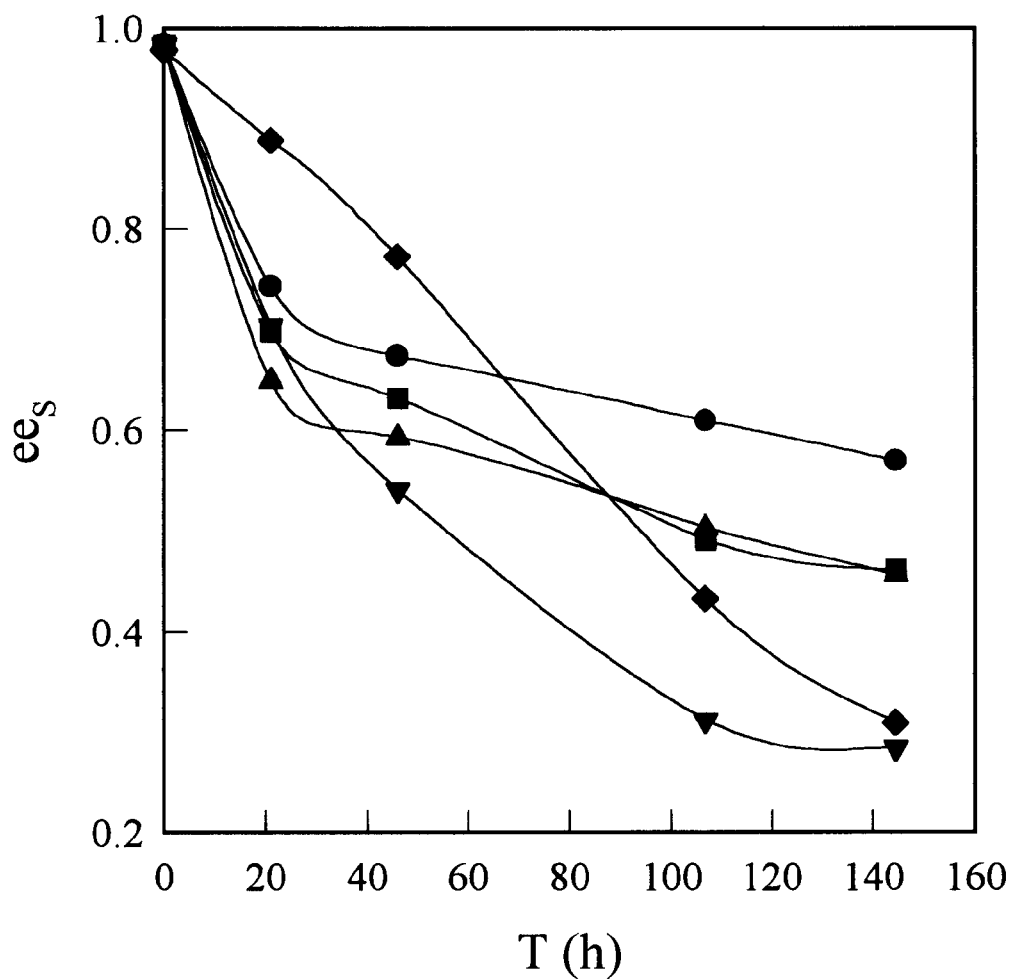
FIG. 4 is a diagram showing the time-course variation of $ee_S$ of (S)-naproxen phenyl thioester in isooctane (meanings of symbols are same as in FIG. 1).

In stead of trioctylamine used as an organic base in Example 1, other inorganic bases such as anion-exchange resin (obtained by modifying IRA 904 anion-exchange resin produced by Sigma Co., USA) could be used to perform effectively the racemization of (R)- or (S)-naproxen thioester. For example, racemization of 1.5 mM (S)-naproxen trifluoroethyl thioester in isooctane containing 230 mM trioctylamine or 10 mg anion-exchange resin at 37° C. resulted in a time-course variation of $ee_S$ shown in FIG. 3; while by using 1.5 mM (S)-naproxen phenyl thioester, resulted in a time-course variation of $ee_S$ shown in FIG. 4.

EXAMPLE 3

Figure 5:
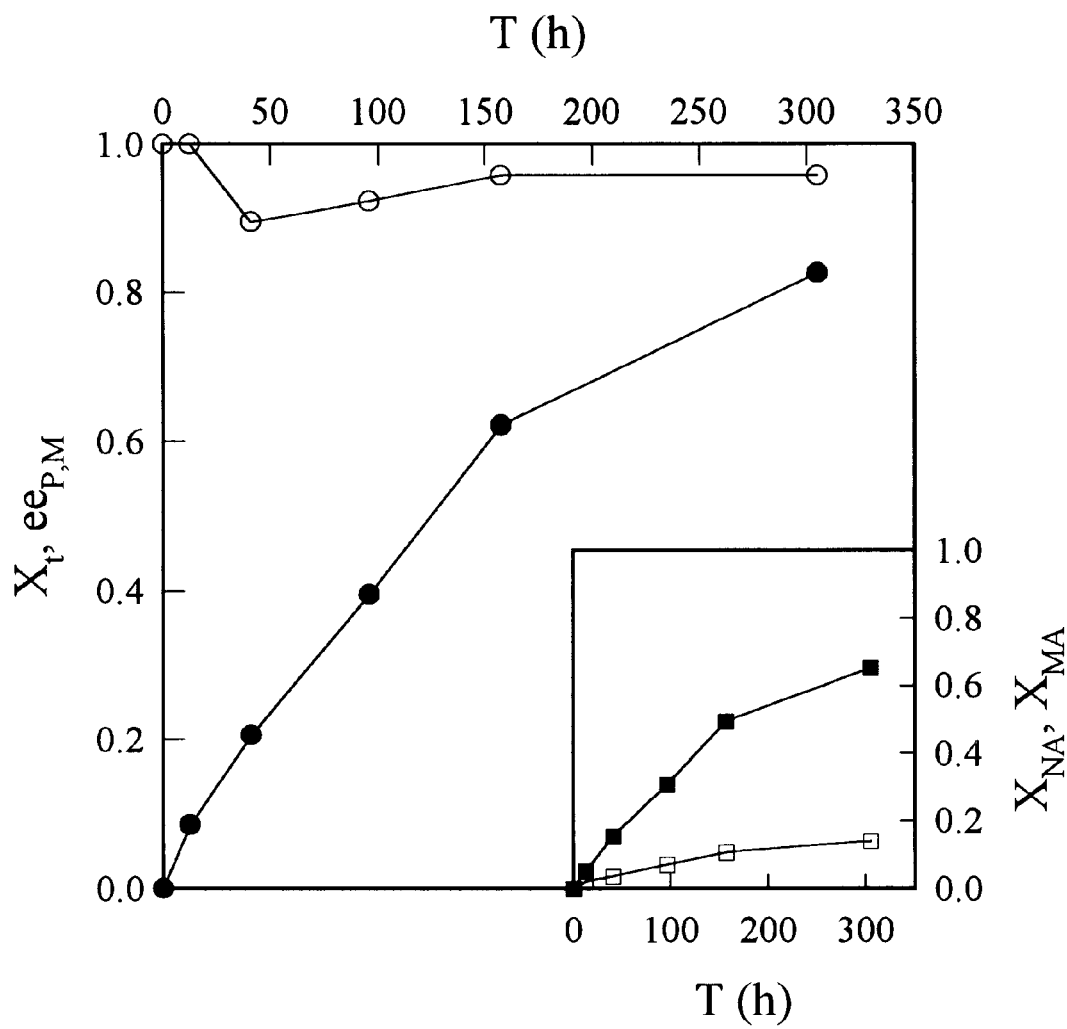
FIG. 5 is a diagram showing the transesterification dynamic resolution of a racemic (S)-naproxen trifluoroethyl thioester: $X_t$, (●); $ee_{P,M}$, (○); $X_{MA}$, (■); $X_{NA}$ , (□).

A series of 15 ml isooctane solution was prepared as containing 3 mM solution of racemic naproxen trifluoroethyl thioester, 50 mM 2-N-morpholinoethanol as the alcohol, 96 mM trioctylamine, and 618 mg polypropylene having Lipase MY immobilized thereto (equivalent to 30 mg/ml Lipase MY) for carrying out transesterification dynamic resolution at 45° C. to synthesize the desired (S)-naproxen 2-N-morpholinoethanol ester prodrug. By taking samples at various time intervals and analyzed by high performance liquid chromatography (mobile phase composition as n-hexane : isopropanol : acetic acid=97:3:1; flow rate=0.4 ml/min, on a Chiralcel OD column provided by Daicel Co., Japan) to obtain time-course variations of the racemate conversion ($X_t$), conversion of hydrolytic by-product of (S)-naproxen ($X_{NA}$), the optical purity ($ee_{P,M}$) and conversion ($X_{MA}$) of (S)-ester product as shown in FIG. 5, wherein $X_t$, $X_{NA}$, $ee_{P,M}$ and $X_{MA}$ are defined as $$X_t = \frac{P_M + Q_M + P_N + Q_N}{A_0 + B_0}$$

$$X_{NA} = \frac{P_N}{A_0 + B_0}$$

$$X_{MA} = \frac{P_N}{A_0 + B_0}$$

$$ee_{P,M} = \frac{P_M - Q_M}{P_M + Q_M}$$

where $A_O$ and $B_O$ represent initial concentrations of (S)-and (R)-naproxen trifluoroethyl thioester, $P_M$ and $Q_M$ represent concentrations of (S)- and (R)-naproxen ester, while $P_N$ and $Q_N$ represent concentration of hydrolytic by-products of (S)- and (R)-naproxen, respectively. In the case of reacting for 303 hours, results of $X_t$=82.6%, $ee_{P,M}$=96% and $X_{MA}$=65% were obtained.

EXAMPLE 4

Procedure described in Example 3 was repeated except that other racemic naproxen thioesters were used as the reaction substrate instead of the racemic naproxen trifluoroethyl thioester, and part of the results of the transesterification resolution were shown in Table 1. When the thiol used for synthesis of thioester has an electronwithdrawing group , such as, 2,2,2-trifluoroethanethiol or thiophenol, the enzyme used exhibited higher activity.

TABLE 1

|  | 105 | | 198 | |
|---|---|---|---|---|
| reaction time (h) | $X_t$(%) | $ee_{P,M}$(%) | $X_t$(%) | $ee_{P,M}$(%) |
| naproxen ethyl thioester | 2.0 | >99 | 2.1 | >99 |
| naproxen propyl thioester | 4.1 | >99 | 5.6 | >99 |
| naproxen butyl thioester | 0.9 | >99 | 1.6 | >99 |
| naproxen phenyl thioester | 37.2 | 98.2 | 41.0 | 97.8 |
| naproxen trifluoroethyl thioester | 28.4 | 93.2 | 33.8 | 91.5 |

Reaction conditions: 15 ml isooctane containing 3 mM racemic naproxen thioester, 10 mM 2-N-morpholinoethanol, 20 mg/ml lipase MY, reaction temperature at 37° C.

EXAMPLE 5

Procedure of Example 3 was repeated except that emzymes from other sources or other solvent shown in Table 2 were used in stead to obtain similar results of transesterification resolution as shown in Table 1.

TABLE 2

| reaction time (h) | 50 | | 200 | |
|---|---|---|---|---|
| | $X_t(\%)$ | $ee_{P,M}(\%)$ | $X_t(\%)$ | $ee_{P,M}(\%)$ |
| lipase MY/isooctane | 32.9 | 95.0 | 58.0 | 92.3 |
| lipase VII/isooctane | 35.2 | 94.8 | 63.0 | 90.9 |
| lipase MY/cyclohexane | 22.3 | 82.6 | 56.7 | 95.2 |
| lipase VII/cyclohexane | 26.4 | 86.4 | 59.6 | 93.8 |

Reaction conditions: 15 ml solvent contains 3 mM racemic naproxen trifluoroethyl thioester, 10 mM 2-N-morpholinoethanol and 20 mg/ml enzyme; reaction temperature at 37° C. Lipase VII produced by Sigma Co. is derived from Candida rugosa having an activity of 1010 mmole/mg/h.

Many changes and modifications in the above described embodiment of the invention can, of course, be carried out without departing from the scope thereof. Accordingly, to promote the progress in science and the useful art, the invention is disclosed and is intended to be limited only by the scope of the appended claims.

What is claimed is:

1. A process for preparing optically active (S)-α-aryl propionic acids and esters thereof, comprising the steps of:
providing a racemic α-aryl propionic acid thioester containing both (R) and (S) racemates, and
carrying out a dynamic resolution on said racemic α-aryl propionic acid by reacting said racemic α-arylpropionic acid thioester with a lipase having (S)-stereoselectivity in the presence of an organic solvent and a base at a temperature of 25 to 70° C., wherein said lipase cleaves (S)-thioester from said racemic α-aryl propionic acid thioester, and said base promotes the simultaneous rapid racemization of unreacted (R)-thioester into said (S)-thioester,
wherein said reaction yields greater than 50% conversion of said racemic α-aryl propionic acid thioester to said (S)-α-aryl propionic acid thioester.

2. A process as recited in claim 1, wherein said racemic α-aryl propionic acid thioester is selected from the group consisting of racemic naproxen trifluoroethyl thioester, racemic naproxen phenyl thioester, racemic naproxen ethyl thioester, racemic naproxen propyl thioester, and racemic naproxen butyl thioester.

3. A process as recited in claim 1, wherein said base used for carrying out said racemization is selected from an organic base and an inorganic base.

4. A process as recited in claim 3, wherein said organic base is trioctylamine, and said inorganic base is an anion exchange resin.

5. A process as recited in claim 1, wherein said racemic α-aryl propionic acid thioester is obtained by reacting α-aryl propionic acid with thiol having an electronwithdrawing group.

6. A process as recited in claim 5, wherein said thiol having electronwithdrawing group is one of 2,2,2-trifluoroethanethiol and thiophenol.

7. A process as recited in claim 1, wherein said lipase has a (S)-stereoselectivity with respect to said racemic α-aryl propionic acid thioester and is derived from *Candida rugosa*.

8. A process as recited in claim 1, wherein said organic solvent is an non-polar solvent selected from isooctane and cyclohexane.

* * * * *